(12) United States Patent
Bell

(10) Patent No.: US 6,228,811 B1
(45) Date of Patent: May 8, 2001

(54) SOLID FORMULATION

(75) Inventor: Gordon Alastair Bell, Maidstone (GB)

(73) Assignee: Zeneca Limited (GB)

( * ) Notice: Subject to any disclaimer, the term of this patent is extended or adjusted under 35 U.S.C. 154(b) by 0 days.

(21) Appl. No.: 09/380,713

(22) PCT Filed: Mar. 2, 1998

(86) PCT No.: PCT/GB98/00644

§ 371 Date: Sep. 3, 1999

§ 102(e) Date: Sep. 3, 1999

(87) PCT Pub. No.: WO98/38853

PCT Pub. Date: Sep. 11, 1998

(30) Foreign Application Priority Data

Mar. 4, 1997 (GB) .................................................. 9704443

(51) Int. Cl.$^7$ .................................................. A01N 25/04
(52) U.S. Cl. .................. 504/366; 504/367; 514/944; 514/947; 424/409
(58) Field of Search .................................. 504/366, 367; 514/944, 947; 424/409

(56) References Cited

U.S. PATENT DOCUMENTS 5,484,600  1/1996  Sjogren ................................. 424/405

FOREIGN PATENT DOCUMENTS

| 3713326A1 | 10/1987 | (DE) . |
|---|---|---|
| 0 699 389 A2 | 3/1996 | (EP) . |
| 2 168 377 * | 6/1986 | (GB) . |
| 4171035A | 6/1992 | (JP) . |
| 7069802A | 3/1995 | (JP) . |
| 7101805A | 4/1995 | (JP) . |
| 7233002A | 9/1995 | (JP) . |
| 8099802A | 4/1996 | (JP) . |
| 8099803A | 4/1996 | (JP) . |
| 8099804A | 4/1996 | (JP) . |

OTHER PUBLICATIONS

Dualite Expanded Polymer Spheres, UCB Chemicals data sheets (1994/95).

O.D. Velev et al., Assembly of Latex Articles by Using Emulsion Droplets as Templates, 12 Langmuir, 2374–2384, (1996).

Okubo & Nakagawa, Formulation of multihollow structures in crosslinked composite polymer particles, 272 Colloid & Polymer Science, 530–535, (1994).

* cited by examiner

Primary Examiner—S. Mark Clardy
(74) Attorney, Agent, or Firm—Thomas R. Savitsky

(57) ABSTRACT

The formation of undesirable sludge in the course of spraying a solution or dispersion of a water-soluble or water-dispersible solid or a structured gel formulation is reduced by the incorporation in the formulation of a low-density solid particulate material having a density of less than one and a diameter of less than the spray nozzle filter through which it will pass. The low-density solid particulate material is preferably a hollow glass or plastic particle having a density of less than 0.8 g/cm$^3$. The invention is particularly applicable to agrochemical formulations.

10 Claims, No Drawings

SOLID FORMULATION

This invention relates to a solid or structured gel formulation and in particular to a solid or structured gel formulation of a water-soluble or water-dispersible material suitable for aqueous spray application after dispersion or dissolution in water. The invention further relates to a method of reducing sludge formation in the course of spraying a solution or dispersion of a water-soluble or water-dispersible solid or structured gel formulation.

Floating granules are known and used for example in paddy water treatments to provide a slow dispersion of material over a passage of time. Such granules are applied directly to the paddy field, as opposed to being tank mixed, and in consequence do not give rise to sludge problems.

In Zasso Kenkyu (1995), 40 (2), 80-6 there is disclosed a study of a naproanilide formulation taking the form of a wettable powder housed in a water-soluble bag and containing hollow glass floating carrier particles. The water-soluble bag containing the formulation is intended for direct application to paddy water. It was concluded that when the concentration of the carrier was high, the formulation floated on the water surface until the wettable powder completely diffused into water and the amount of naproanilide released from the formulation into water was large. If the concentration of the carrier was low, the entire body of the formulation sank soon after the film dissolved in water resulting in low release of naproanilide. In tests of biological activity it was concluded that a wettable powder packed in a water soluble film containing 20% floating carrier has potential as a formulation which could reduce the labour of herbicide application in paddy fields but that when the carrier content was less than 14%, little amount of naproanilide diffused in the water and the herbicidal efficacy was extremely low.

The present invention is applicable to any solid or structured gel formulation suitable for aqueous spray application after tank mix dispersion or dissolution. Whilst the present invention is not restricted to any one particular field, such solid or structured gel formulations are typically used for aqueous sprays in agriculture, public health and animal health. Thus the active ingredient may for example be a herbicide, insecticide, nematocide, fungicide or plant growth regulator. Alternatively the granule may be used to carry an auxiliary agent such as a wetter or other adjuvant.

Active ingredients or auxiliary agents suitable for application by means of an aqueous spray may be formulated in a wide variety of ways. The present invention relates to solid water-soluble or water-dispersible formulations such as granule formulations (sometimes also referred to as water-soluble or water-dispersible grain formulations or wettable granules). The present invention is not however limited to granule formulations its advantages may also be apparent in other forms of solid formulation such as "cast tapes" (as described for example in International application No 96/02947 and in GB 2095558), flakes, wettable powders or tablets. The present invention also relates to structured gel formulations, for example structured gel formulations suitable for incorporation in a water-soluble bag and containing solid water-dispersible material.

Such solid or structured gel formulations (and in particular structured gel formulations when housed in a water-soluble bag) have a number of advantages as compared with liquid formulations. Such advantages include for example reduced transport costs, reduced operator exposure and reduced residue contamination of containers. A solid formulation or water-soluble bag containing a structured gel formulation may reduce residue formation to the extent that the use of a disposable container is acceptable.

A wettable, dispersible or water-soluble solid or structured gel formulation normally consists of an agrochemical or other ingredient suitable for application by aqueous spray incorporated with a solid inert filler which may be water-soluble or water-dispersible. The agrochemical or other ingredient may be a solid or liquid and may be water-soluble or water-dispersible. Auxiliary agents such as surfactants, activity enhancers, anti-foams and stabilisers are frequently used and may be incorporated in the same solid or structured gel formulation with the active ingredient or may be formulated separately or may be added at the tank mix stage.

Solid or structured gel formulations such as granules may be formed by a variety of techniques, including for example pan granulation, spray drying, agglomeration and extrusion. Techniques for providing solid "cast tapes" are illustrated in GB 2095558 and in our International application No 96/02947. Techniques for providing structured gel formulations are illustrated for example in WO 96/03871.

In use, the solid or structured gel formulation is added to water to form a solution or dispersion which is then applied as a spray, for example as a spray application to plants. In agrochemical use for example, the solid or structured gel formulation is typically mixed immediately prior to spraying with water in a tank containing from about 20 liters for a knapsack sprayer to about 100 to 2000 liters of water for a commercial spray tank. The structured gel formulation may conveniently be housed in a water-soluble bag prior to addition to water. Solid formulations are more normally added directly to the water but may also be housed in a water-soluble bag if desired. Whilst such spray tanks are generally provided with some means of agitation, such as mechanical stirring or pumped circulation of the water, the degree of mixing within the tank may be relatively inefficient or the solid or structured gel formulation itself may be inherently difficult to disperse, particularly for example if the formulation has been allowed to age. In particular there may be specific zones within the tank ("dead zones") in which the level of agitation is especially poor. In practice therefore effective dispersion of insoluble or partially or slowly soluble materials may not be achieved and an insoluble solid sludge may build up in such dead zones within the tank during the time-scale of spray application. Once a sludge is allowed to start to build up, it may become compacted and much harder to re-disperse, even with the application of effective agitation. Even if the sludge is re-dispersed, it may still form relatively large agglomerates of particles which may tend to block the spray nozzles or filters. Furthermore, the formation of a sludge represents a removal of active material from the aqueous phase leaving the spray nozzle. Thus even if the sludge is eventually dispersed and leaves no residue, the concentration of active material in the spray will be less in the initial stages than in the later stages when the sludge is beginning to break up and pass through the nozzle. Sludge formation can therefore lead to uneven distribution of the active ingredient in the spray and poor biological utilisation of active material. Sludge left in the spray tank after spraying is completed may cause contamination and disposal problems. In general the formation of sludge in the spray tank is a well-recognised problem which may be associated with the use of solid or structured gel formulations. One solution to this problem would of course be to provide more efficient agitation within the mixing tank but the cost involved makes this unattractive and a solid or structured gel formulation having reduced sludge formation in conventional spray tanks is to be preferred.

We have now found that the problem of sludge formation may be mitigated if the density of the solid or structured gel formulation is reduced by the incorporation therein of a solid particle hang a density of less than one. Since the solid particle should not block the nozzle it should have a diameter less than that of the spray nozzle. Furthermore since in use the spray nozzle is generally protected from blockage by a suitable filter, the particle should preferably have a diameter of less than of the spray nozzle filter through which it will pass.

Thus according to the present invention there is provided a method of reducing sludge formation in the course of spraying a solution or dispersion of a water-soluble or water-dispersible solid or a structured gel formulation which comprises incorporation in said solid or structured gel formation a low-density solid particulate material having a density of less than one g/cm$^3$ and a diameter of less than the spray nozzle filter through which it will pass.

According to a further aspect of the present invention there is provided a solid or a structured gel formulation suitable for use in such a method comprising a low-denay solid particulate material having a density of less tan one g/cm$^3$ and a diameter of less than the spray nozzle filter through which it will pass.

The solid or structured gel formulation will normally be water-dispersible since the problem of sludge formation is clearly less serious with water-soluble solid or structured gel formulation, although even water-soluble solid or structured gel formulations may give rise to sludge formation if the dissolution of the solid is slow compared with the of spraying. Thus for example a typical solid formulation of the invention is a water-dispersible granule, powder, flake, tablet or cast, tape and comprises a water-dipersible or water-soluble agrochemical or agrochemical auxiliary agent and a water-dispersible carrier. A typical structured gel will contain water-dispersible material held within the gel structure.

Problems of sludge formation are most commonly associated with the use of a water-dispersible filter. Many such filters are known in the art and a wide commercial choice of filter is available. Examples of typical water-dispersible filters include talc, silica, kaolin, pyrophylite, powdered limestone, acid clay, ditamaceous earth, gypsum, pumice, shell powder, mica and silicates. Dense water-dispersible fillers such as talc may give rise to particular problems by propelling granules rapidly to the floor of the spray tank to form difficult sludges.

The low-density solid particular material having a density of less than one g/cm$^3$ preferably has a density of less than 0.8 g/cm$^3$ for example less than 0.3 g/cm$^3$ and preferably less than 0.2 g/cm$^3$ for example about 0.1 g/cm$^3$. Unless otherwise stated the units of density used herein in respect of the low-density solid particulate material are g/cm$^3$. Such low densities are conveniently achieved by use of a hollow particle, and the solid particulate material having a density of less than one is preferably a hollow particle, for example a hollow glass or plastics particle. An especially suitable material comprises expanded polymer microspheres which in general have a lower density than hollow glass particles. Suitable expanded polymer spheres are available under the trademark "Dualite" from UBC (Chem) Limited, a product of Pierce & Stevens. A suitable polymer material is a polyvinylidene chloride acrylonitrile co-polymer, an acrylonitrile co-polymer a polystyrene polymer or a poly (vinylidene chloride) polymer. The low-density solid particulate material may be supplied with inorganic filler particles, for example calcium carbonate, embedded in the surface. Whilst this is not believed to be essential for the purposes of the present invention, no adverse consequences have been observed if a surface-coated product is used.

The low-density solid particulate material preferably passes completely through a BS standard 100 mesh sieve (BS No 410/1986-150$\mu$), and for example has a volume mean diameter (D(4,3)) below 100 microns, for example below 50 microns. Preferably the material has a volume mean diameter between 20 to 50 microns, for example from 20 to 30 microns. Finer particles may be used if desired but may be more difficult to formulate satisfactorily. Particles having a diameter between 50 and 100 microns or more have been found to be effective in achieving sludge reduction in the method of the invention but may cause filter blockage in those applications in which a relatively fine filter is required. For such applications, it is especially preferred that the low-density solid particulate material has a volume size distribution such that 5 volume percent has a size no greater than about 60 microns and more preferably no greater than about 50 microns.

The proportion of low-density solid particulate material to be used depends to some extent on the overall density of the solid or structured gel formulation and in particular the nature of the water-dispersible filler in the solid or structured gel formulation. In general the low-density solid particulate material may comprise from about 0.01 to about 10% by weight of the total solid or structured gel formulation and preferably from about 0.1 to about 6% by weight, for example from 0.1 to 2% by weight of the total solid or structured gel formulation. There is clearly no particular advantage in including a greater proportion of low-density solid particulate material than that required to make the solid or structured gel formulation float. Furthermore, we have found that it is not necessary, and indeed may be positively undesirable to include sufficient low-density solid particulate material that the solid or structured gel formulation actually floats. Thus although a solid or structured gel formulation which floats prior to dissolution in the spray tank may be used, it is preferred that sufficient of the low-density particulate material is used such that the solid or structured gel formulation sinks slowly on addition to water i.e. that there is added less low-density solid particulate material than the quantity which would be required to make the water-soluble or water-dispersible solid or a structured gel formulation float in water. If a solid or structured gel formulation is used in a water-soluble bag, the bag and content may of course initially float when added to water, provided that when the contents are eventually released from the bag they sink slowly.

Very low density granules are also not generally preferred for practical reasons because they tend to exhibit poor packing characteristics. The packing of a solid formulation may be measured in terms of its "tap density" which is the volume occupied by the solid formulation in a container (such as a measuring cylinder) after gentle tapping to allow the solid to settle divided by the weight of the solid. A tap density of between 0.25 to 0.6 g/ml is preferred. Granules having a tap density of about 0.35 g/ml will generally just float in water and the tap density is more preferably from about 0.35 to about 0.5 g/ml for granules of the invention. Other formulations such as cast tapes exhibit much better packing than granules and the tap density of cast tapes may therefore be higher. Since there are essentially no air spaces in cast tape formulations, tapes will normally just float at a "tap density" of one (i.e. the "tap density" is the same as the true density). Typical cast tapes of the invention may have a density in the range from 0.5 to 1.7 g/ml and preferably 1 to 1.6 g/ml. At least a part of the function of the low-density solid particulate material is believed to be a result of the reduction in the overall density of the solid or structured gel formnulation, for example the granule or tape, which prevents it sinking rapidly to the floor of the spray tank immediately on addition. However, although the function of the low-density solid particulate material in reducing sludge is poorly understood, it is believed to be more complex than a simple reduction in density. Thus for example individual particles of low-density solid particulate material are believed to break away from the surface of the dispersing solid or structured gel formulation and rise rapidly to the water surface, thereby facilitating the break-up of the surface of the solid or structured gel formulation and creating additional turbulence in the spray tank.

The solid or structured gel formulation, such as the granule or cast tape, may contain one or more active ingredients or auxiliary agents and may contain one or more additional components such as a synergist, a humectant, a dye, a pigment, a corrosion inhibitor, a wetting agent or a dispersing agent. It will generally be desirable, but not essential, to include a wetting agent or a dispersing agent in the granule.

Wetting or dispersing agents include cationic, anionic or non-ionic agents. Suitable cationic agents are quaternary ammonium compounds, for example, cetyltrimethylarnmonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide.

The low-density solid particulate material may be incorporated into the solid or structured gel formulation along with the other solid ingredients and using conventional methods known to those skilled in the art for preparing such formulations.

The invention is illustrated by the following Examples in which all parts and percentages are by weight unless otherwise stated.

EXAMPLE 1

Granules containing 50% by weight of the commercial insecticide pirimicarb were prepared by conventional extrusion techniques except that there was added 5% by weight of a low-density solid particulate material commercially available under the trademark "Dualite" M6033AE consisting of expanded polyvinylidene chloride acrylonitrile copolymer spheres having a density of about 0.13, a mean particle size of 25 microns and a size distribution such that 5% by volume had a diameter greater than 43 microns. A commercially available granule (950 g), "Pirimor" 50 WG ("Pirimor" is a trademark of Zeneca Limited and contains primicarb as active ingedient) was ground to a powder and low-density solid particulate material (50 g) was added. Water (140 g) was added and the mixture was blended in a Hobart mixer to form a smooth paste which was granulated by extrusion through a 1 mm sized screen. The resultant granules were dried at 50° C. for 20 minutes.

The granules of the invention were compared with granules prepared in exactly the same way by grinding "Pirimor" 50 WG and subsequent re-granulation but in which the low-density solid particulate material was omitted.

The granules were added to 800 liters of water in a commercial Horstine Farmery 1000 liter tank agricultural spray tank with conventional agitation supplied by a re-circulation pump to give a theoretical concentration of active ingredient (pirimicarb) equivalent to 0.44 g/l assuming the product completely dispersed. Both the granules of the present invention and granules not containing the low-density solid particulate material sank on addition to water. The resultant dispersion was sprayed through an elliptical nozzle of approximately 450 micron diameter (more specifically defined as BCPC Fan 110° at 0.8 liters per minute and 3 bar pressure) protected by a 150µ micron filter. The uniformity of the spray was determined by measuring the concentration of pirimicarb in the spray solution at intervals corresponding to the removal by spraying of 100 liter aliquots from the tank. The results are given in Table 1 from which it will be seen that a significantly more uniform spray gradient is obtained using the granules of the invention compared with granules not containing low-density solid particulate material.

After spraying was completed the residue in the tank was collected. Visual inspection showed that the sample which contained the low-density solid particulate material had left a slight residue on the base of the tank but this was significantly lower than from the control experiment.

TABLE 1

| | Granule of the invention containing low-density solid particulate material | | Corresponding granule without low-density solid particulate material | |
|---|---|---|---|---|
| Liters Sprayed | Concentration of pirimicarb (g/l) | Deviation from theoretical concentration | Concentration of pirimicarb (g/l) | Deviation from theoretical concentration |
| 0 | 0.46 | 0.02 | 0.43 | −0.01 |
| 100 | 0.47 | 0.03 | 0.44 | 0.00 |
| 200 | 0.48 | 0.04 | 0.43 | −0.01 |
| 300 | 0.58 | 0.14 | 0.43 | −0.01 |
| 400 | 0.59 | 0.15 | 0.42 | −0.02 |
| 500 | 0.55 | 0.11 | 0.48 | 0.04 |
| 600 | 0.63 | 0.19 | 0.58 | 0.14 |
| 700 | 0.60 | 0.16 | 0.73 | 0.29 |
| 800 | 0.59 | 0.15 | 0.82 | 0.38 |

EXAMPLE 2

Granules containing 50% by weight of the herbicide fluazifop-p-butyl and 5% by weight of "Dualite" M6033 AE were prepared in the same manner as in Example 1 from a commercially available granule. A control formulation was prepared which did not contain the "Dualite" M6033 AE but was identical in respect of the other formulation ingredients. The samples were sprayed in a 1000 liter Horstine Farmery agricultural spray tank at a nominal concentration of 1.875 g/l, which was formed by the addition of 3 kilos of the granules to 800 liters of water. Samples of the spray solution showed that the inclusion of the "Dualite" M6033 AE had improved the concentration gradient compared to the control sample. Examination of the base of the tank after spraying was complete showed that there was no observable residue present from the sample containing "Dualite" M6033 AE whilst the control sample left a residue which was estimated to contain 50% by weight of the starting granules.

EXAMPLE 3

Granules containing 50% by weight of the commercial insecticide pirimicarb were prepared by conventional extrusion techniques, except that there was added 2% by weight of low density solid particulate material commercially available under the trademark "Dualite" M6033AE as used in Example 1.

A commercially available granule (735 g), "Aphox" 50 WG ("Aphox" is a trademark of Zeneca Limited) was ground to a powder, and low density solid particulate material (15 g—to provide 2% w/w "Dualite" in the final granule) was mixed in. Water (180 g) was added and the mixture blended in a Hobart mixer to form a smooth paste which was granulated by extrusion through a 1 mm sized screen. The resultant granules were dried at 50° C. for 20 minutes. This batch procedure was repeated several times in order to produce the quantity of granules required for testing. The above procedure was repeated with "Aphox" granules (720 g) and low density solid particulate material (30 g), to produce "Aphox" 50 WG containing 4% w/w "Dualite". Finally, a control sample was produced in exactly the same way by grinding "Aphox" 50 WG and subsequent re-granulation but in which the low density solid particulate material was omitted. All granules sank on addition to water.

Sludge formation was evaluated using a laboratory sludge test which has been found to simulate commercial large scale spray application. The test, designed to measure the amount of sludge that is left in the bottom of a glass beaker after the granules have been allowed to disperse without agitation for 10 minutes was carried out as follows:

Sludge Test

A dry 600 ml glass beaker is weighed (X g) and about 300 g of water is added. The water will normally be from a sink tap and it is necessary that the temperature of the water is recorded. About 50 g (Z g) of granule product is weighed accurately and added to the water. The granules are left immersed in the water for 10 minutes without agitation. The contents of the beaker are poured into an effluent container, after allowing 30 seconds for drainage of the residue from the upturned vessel. The beaker is then transferred to an oven at 50° C. in order to dry the wet residue. After 30 minutes (or when the residue is dry) the mass of the glass beaker plus residue (W) is determined.

The initial sludge residue (%) is then quoted as: $(W-X/Z) \times 100$

The sludge test results for the above WG formulations are given in Table 2:

TABLE 2

| Low Density particulate Material (%) | Sludge (%) | Temp (° C.) |
|---|---|---|
| 0 | 3.0 | 21.5 |
| 2 | 2.8 | 21.5 |
| 4 | 1.6 | 21.5 |

Spray tests on the above WG formulations were carried out as follows:

Spray Test

The test granules (1 kg) were added to 400 liters of water in a commercial Horstine Farmery 1000 liter agricultural spray tank with conventional agitation supplied by a re-circulation pump. The granules sank to the base of the tank and dispersed in the agitated water. The resultant dispersion was sprayed through four elliptical nozzles of approximately 450 micrometer diameter. Two of the four nozzles were protected by 150 micrometer filters, and the other two by 300 micrometer filters. The uniformity of the spray was determined by taking 250 ml spray samples at intervals corresponding to the removal by spraying of 100 liter aliquots from the tank. The spray samples were visually inspected for turbidity and graded by comparing to 3 pre-prepared calibration spray samples, where 10/10 was the grade given for an expected spray concentration (0.63 g/250 ml), 5/10 was the grade given for a spray concentration half that of the expected spray concentration (0.31 g/250 ml) and 20/10 was the grade given for a spray concentration twice that of the expected spray concentration (1.25 g/250 ml).

The results of the spray tests are shown in Table 3 from which it can be seen that a significantly more uniform spray gradient is obtained using the granules of the invention compared with the granules not containing the low density solid particulate material.

TABLE 3

| Volume Sprayed (liters) | Granule of the invention containing 4% w/w low density solid particulate material Grade | Corresponding granule without low density solid particulate material Grade |
|---|---|---|
| 0 | 9/10 | 6/10 |
| 100 | 10/10 | 6/10 |
| 200 | 10/10 | 7/10 |
| 300 | 10/10 | 15/10 |
| 400 | 10/10 | 20/10 |

After spraying was completed the spray nozzles were checked for blockages and residue and the base of the spray tank inspected for sludge residue. The results are shown in Tables 4 and 5 respectively.

TABLE 4

| Nozzle | Filter Size (μm) | Granule of the invention containing 4% w/w low density solid particulate material Assessment | Corresponding granule without low density solid particulate material Assessment |
|---|---|---|---|
| 1 | 300 | none | none |
| 2 | 150 | trace | 5% residue |
| 3 | 300 | trace | trace |
| 4 | 150 | 5% residue | 30% residue |

TABLE 5

| Low Density Solid (%) | Sludge Residue (%) | Temperature (° C.) |
|---|---|---|
| 0 | 5–10 | 25 |
| 2 | 2 | 24 |
| 4 | 1 | 25 |

Bioefficacy Test

Glasshouse tests confirmed that the polymeric low-density, microparticles do not adversely affect the bioefficacy of "Aphox" WG formulations. Standard glasshouse aphid contact/residual tests carried out on a mixed age population of R2 *Myzus persicae* showed that the re-extruded "Aphox" WG formulation with "Dualite" M6033AE, demonstrates aphicidal activity that is not statistically different from the commercial "Aphox" 50 WG formulation.

EXAMPLE 4

A solid formulation in the form of a water dispersible tape comprising approximately 5% by weight of lambda-cyhalothrin and 0.16% by weight of low density solid particulate material commercially available under the trademark "Dualite" M6033AE as used in Example 1 was prepared according to the following procedure:

A mixture of polyvinylpyrrolidone polymers of molecular weights 10,000 (5.80 g) and 44,000 (2.80) was added to water (19.90 g) and stirred until all the polymer had dissolved. "Morwet" EFW (0.20 g) an anionic naphthalene sulphonate wetting agent from Witco, and Microtalc filler (17.10 g) a hydrated magnesium silicate with a mean particle size of approximately 7 micrometers, were added and stirred until all the powder was completely dispersed. Sorbitol (2.50 g), silicone antifoam (0.15 g), lambda-cyhalothrin (1.50 g) and "Dualite" M6033 AE (0.05 g) were finally mixed in and stirred for a further 15 minutes to ensure complete dispersion.

The viscous film-forming slurry was cast onto a polymer film substrate, using a 'doctor blade' set at a blade height of 0.75 mm. The cast tape was dried for 2 hours in an oven maintained at 50° C. and then stripped from the substrate as a coherent tape of thickness 0.31 mm. 10 g of the tape was then cut into 20 squares of dimension 20×20 mm. The density of the tape was 1.426 $gm^{-3}$ (greater than the density of water). The tape samples were then spray tested in a Coopler Pegler CP3 knapsack sprayer, The tapes were added to the spray tank which was filled with 4 liters of water at 9.5° C., and allowed to soak for 1 minute. The tank was then topped up to 20 liters of water and shaken 10 times from side to side, prior to spraying. Spray samples were examined when the water level in the tank was 20, 16, 12, 8, 4 and 1 liter. No nozzle blockage occurred during spraying, the spray samples examined were essentially uniform in colour and no tape residue was present in the base of the tank when spraying was complete.

In comparison, spray testing of a control water dispersible tape sample prepared in exactly the same manner but in which the "Dualite" powder was omitted showed a sludge residue of 5–10% at the base of the tank.

EXAMPLE 5

A gel formulation comprising 62.5% w/w fluazifop-P-butyl was prepared according to the procedure described in Example 1 of International application WO 96/03871. The composition of the gel was as follows:

| Component | Amount (% w/w) |
|---|---|
| Fluazifop-P-butyl | 62.5 (amount of active ingredient present) |
| Methyl oleate | to 100 |
| Silica power (surface area 200 $m^2/g$) | 2.0 |
| BRIJ 96 | 1.0 |
| Ethylene glycol | 1.0 |
| SYNPERONICA4 | 2.0 |
| SOPROPHOR 4D 384 | 2.0 |
| AEROSOL OT-B | 2.5 |
| Phenyl sulphonate CALX | 1.0 |

(BRIJ, SYNPERONIC, SOPROPHOR and AEROSOL are trademarks or tradenames) The ingredients listed were sequentially added (in the order listed) and high shear mixed to produce a homogeneous gel. The low-density solid particulate material "Dualite" M6033AE (0.8 g) was then added to the fluazifop-P-butyl 62.5 gel formulation (39.2 g) and stirred in using a spatula to produce a homogeneous gel comprising 2% by weight of low-density solid particulate material. The formulation was then left to stand overnight, to allow the gel structure to reform.

When added to water, the gel formulation according to the invention sank slowly. When tested according to the sludge test procedure described in Example 3, the gel formulation according to the invention produced 0.7% sludge when immersed in water at 21° C., whilst the comparison gel not containing low-density solid particulate material produced 7.6% sludge.

EXAMPLE 6

A tablet formulation containing "Fordacal" 30 (1.8 g), a powder comprising crystalline calcium carbonate of mean particle size 7 micrometers, and "Igepal" CO-990 (0.1 g), a nonyl phenol ethoxylate surfactant, and "Dualite" M6017 AE (0.1 g), polymeric microspheres having a mean particle size of 70 micrometers, was produced by mixing the three powder components and compressing in a 'Specac' tablet compactor for 1 minute under a force of 10 tons. The resultant tablet (comprising 5% by weight of the polymeric microspheres) had a diameter of 25 mm and a thickness of 2.1 mm. A control tablet, comprising "Fordacal" 30 (1.9 g) and "Igepal" CO-990 (0.1 g) and no "Dualite" component, was also produced in a similar manner.

The two tablets were immersed in separate 400 ml beakers containing water (300 ml) at a temperature of 22° C. and both sank. After 2 minutes of soaking the tablet containing the "Dualite" microspheres showed faster disintegration and dispersion in comparison to the control tablet.

EXAMPLE 7

A wettable powder (WP) formulation (comprising 1.5% by weight of low-density microparticles) contained in a water soluble bag was prepared as follows. Pre-ground N-phosphonomethylglycine acid powder (500 g, active ingredient content), "Dualite" M6033 AE (15 g) and pre-ground "Igepal" CO990 (to 1 kg), a nonyl phenol ethoxylate surfactant, were mixed to form a homogeneous blend. The powder blend (113 g) was weighed into a water soluble bag (Chris Craft Grade M7031, 38 micrometer thick sachets of dimension 3× 3 inches) and heat sealed using an impulse heat sealer. Two similar bags were prepared and stored in sealed polythene/polyamide laminated outer packs.

A further two bags were prepared in exactly the same manner as above except that the low-density "Dualite" powder was omitted.

Spray tests on the formulations were carried out as follows:

A commercial Horstine Farmery 1000 liter agricultural spray tank was filled to 100 liters with water at 20° C. The water was agitated by means of a re-circulation pump whilst the sachets, added through the top opening of the tank, were allowed to rupture under the action of the water. Once the sachets had ruptured, the wettable powder which was released sank. After mixing for a further 2 minutes, the water was topped up to 400 liters and allowed to mix for a further 1 minute prior to spraying.

The bags containing the formulation of the invention resulted in good dispersion of the product with no tank or sieve residue. In the case of the control samples (without added "Dualite"), some 50% of the product remained as residue in the tank.

EXAMPLE 8

An "Aphox" granule formulation comprising 2% w/w of a larger diameter, low-density solid particles—"Dualite" M6017 AE, consisting of expanded polyvinylidene chloride acrylonitrile copolymer spheres having a density of 0.13 g/cm$^3$ and a mean particle size of 70 microns—was prepared according to the procedure described in Example 3. Spray tests carried out according to the procedure described in Example 3 gave no nozzle blockage during spraying, produced spray samples that were essentially uniform in colour and showed only a small amount of residue (less than 2%) at the base of the tank on completion of the spray cycle.

EXAMPLE 9

A solid formulation in the form of a water dispersible tape was prepared as follows: Polyvinylpyrrolidone polymer of molecular weight 10,000 (17.2 g) was added to water (39.9 g) and stirred until all the polymer had dissolved. "Morwet" EFW (0.4 g) an anionic naphthalene sulphonate wetting agent from Witco, and Microtalc filler (34.2 g) a hydrated magnesium silicate with a mean particle size of approximately 7 micrometers, were added and stirred until all the powder was completely dispersed. Sorbitol (5.0 g) and silicone antifoam (0.3 g), and "Tecfil" T85LD (3.0 g), an alumino silicate glass from Filtec Ltd, composed of hollow, free flowing spheres of density 0.5 g/cm$^3$ with at least 99% of the particles less than 85 micrometer in diameter, were finally mixed in and stirred for a further 15 minutes to ensure complete dispersion.

The viscous film-forming slurry was cast onto a polymer film substrate, using a 'doctor blade' set at a blade height of 0.75 mm. The cast tape was dried for 2 hours in an oven maintained at 50° C. and then stripped from the substrate as a coherent tape comprising 5% by weight of glass microspheres. A control water dispersible tape sample, was prepared in exactly the same, but without the addition of the low-density "Tecfil" T85LD powder. The two tape samples were immersed in separate 400 ml beakers containing water (300 ml) at a temperature of 22° C. Both tapes sank, but the tape containing the "Tecfil" microspheres immediately showed release of low-density microspheres on soaking which resulted in faster disintegration and dispersion in comparison to the control tape.

What is claimed is:

1. A method of reducing sludge formation in the course of spraying a solution or dispersion of a water-soluble or water-dispersible solid or a structured gel formation of a water-dispersible or water-soluble active agent for use in agriculture, public health or animal health or an auxiliary agent for use in such fields which method comprises a) incorporating in said solid or structured gel formulation a low-density solid particulate material having a density of less than one g/cm$^3$ and a diameter of less than the spray nozzle filter through which it will pass b) adding said solid or structured gel formulation to water in a spray tank to form a solution or dispersion of the active agent or auxiliary agent and c) applying said solution or dispersion to plants as a spray via a spray nozzle filter and spray nozzle.

2. A method according to claim 1 wherein the water-soluble or water-dispersible solid formulation is a water-dispersible granule or cast tape.

3. A method according to claim 1 wherein the low-density solid particulate material is a hollow glass or plastics particle having a density of less than 0.8 g/cm$^3$.

4. A method according to claim 4 wherein the low-density solid particulate material has a density of less than 0.2 g/cm$^3$.

5. A method according to claim 1 wherein there is added less low-density solid particulate material than the quantity which would be required to make the water-soluble or water-dispersible solid or a structured gel formulation float in water.

6. A method according to claim 1 wherein the low-density solid particulate material comprises from 0.01 to about 10% by weight of the total solid or structured gel formulation.

7. A method according to claim 6 wherein the low-density sold particulate material comprises from 0.1 to about 6% by weight of the total solid or structural gel formulation.

8. A method according to claim 1 wherein the low-density solid particulate material has a volume mean diameter below 100 microns.

9. A method according to claim 8 wherein the low-density solid particulate material has a volume mean diameter of from 20 to 50 microns.

10. A method according to claim 1 wherein the water-soluble or water-dispersible solid or structured gel formulation contains a water-dispersible or water soluble filler.

* * * * *